US00PP08755P

United States Patent [19]

Hayes, deceased

[11] Patent Number: Plant 8,755

[45] Date of Patent: May 31, 1994

[54] CHUCK HAYES GARDENIA

[76] Inventor: Charles J. Hayes, deceased late of Kitty Hawk, N.C.; Charles J. Hayes., Jr., (executor) P.O. Box 229, Kitty Hawk, N.C. 27949

[21] Appl. No.: 3,097

[22] Filed: Jan. 11, 1993

[51] Int. Cl.[5] ..... A01H 5/00
[52] U.S. Cl. ..... Plt./67.6
[58] Field of Search ..... Plt. 67.6

*Primary Examiner*—James R. Feyrer
*Attorney, Agent, or Firm*—Breiner & Breiner

[57] ABSTRACT

The invention relates to a new and distinct variety of *Gardenia jasminoides* which originated as a seedling selected from a cultivated seedling population. The new variety is characterized by a resistance to cold, tolerance of warmer temperatures resulting in longer blooming periods, high floriferousness, and a compact, condensed appearance.

2 Drawing Sheets

BRIEF DESCRIPTION OF THE INVENTION

The present invention relates to a new and distinct variety of hardy *Gardenia jasminoides*, which is characterized by its resistance to cold temperatures, a tolerance for warmer temperatures resulting in longer blooming periods, high floriferousness and compact, condensed appearance.

All observations and measurements of the Chuck Hayes Gardenia were recorded at the Hampton Roads Agricultural Experiment Station in Virginia Beach, Va.

The new variety of gardenia plant known as the Chuck Hayes Gardenia was selected as the hardiest of a cultivated seedling population. Seeds and seedlings were collected from various species of *Gardenia jasminoides* from the landscape in North Carolina and cultivated. The seed from which the Chuck Hayes Gardenia originated was one of these plants. The specific parent plant, however, of the Chuck Hayes Gardenia is unknown. The Chuck Hayes Gardenia was asexually propagated with vegetative or shoot-tip cuttings. Asexual propagation occurred at Hampton Roads Agricultural Experiment Station in Virginia Beach, Va. using a ventilated, high humidity propagation system. The Chuck Hayes Gardenia has a higher tolerance to temperature extremes as compared to other varieties of gardenia, such as the gardenia "Mystery".

*Gardenia jasminoides* "Mystery" is considered a hardy variety of gardenia plant and is commonly used in landscaping in cooler climates because of its resistance to cold. "Mystery" was observed to freeze in the field at 5° F. with 60% dieback while the Chuck Hayes Gardenia lost only a few leaves on the windward side. Under laboratory testing, "Mystery" shoot tips were extensively damaged at −5° F. without recovery. The Chuck Hayes Gardenia shoot tips survived the same temperature with no damage and recovered new shoot growth. Neither cultivar was damaged at 0° F.

The Chuck Hayes Gardenia also displays a higher tolerance to warmer temperatures during blooming periods than other varieties of gardenia. Most varieties of gardenia abort their buds during blooming periods when evening temperatures reach 65° F. The Chuck Hayes Gardenia, however, tolerates evening temperatures of 70° F. before bud abortion occurs. As a result, unlike other varieties of gardenia, the Chuck Hayes Gardenia continues to bloom into the latter weeks of June.

The average blooming period for most varieties of gardenia is one to two weeks in June. The Chuck Hayes Gardenia, however, blooms continuously for three to four weeks during June and produces up to four times as many flowers per plant as compared to other varieties of gardenia. In addition, the Chuck Hayes Gardenia displays an insensitivity to day lengths which allows it to continue to flower during the fall cool season. Approximately 500 flowers opened on the original Chuck Hayes Gardenia during the September season and continued to bloom until the October frost.

The Chuck Hayes Gardenia is a robust plant. The Chuck Hayes Gardenia matures as a shorter plant, i.e., 3–4 feet in height, as compared to the species, i.e., 6 feet. However, the Chuck Hayes Gardenia grows more rapidly until it matures. Rooted cuttings grow to 1 to 1.5 feet multi-stemmed plants in one growing season. Additionally, the Chuck Hayes Gardenia has broader leaves than "Mystery" making it more attractive than "Mystery". The growth habit of the Chuck Hayes Gardenia in relation to its physical characteristics include a spread which is slightly wider than tall, i.e., a 3 feet tall plant is about 4 feet wide. Branching of the Chuck Hayes Gardenia is dichotomous, i.e., branching is from each side of a terminal flower bud. The internode length of the Chuck Hayes Gardenia is shorter, about 1 to 2 inches, than the internode length of "Mystery" which is about 1.5 to 2.5 inches. The internode length of the Chuck Hayes Gardenia shortens upon maturity of the plant. In mature plants, the internode length varies between $\frac{1}{8}$ to $\frac{3}{4}$ inches. With regard to the density of branching, the Chuck Hayes Gardenia stems are thicker and stiffer than the stems of "Mystery" which have thin, flexible stems. The canopy of most gardenias is relatively compact. The shorter leaf of the Chuck Hayes Gardenia is offset by the greater number of leaves per length of stem.

Unlike other varieties of gardenia, the Chuck Hayes Gardenia tolerates exposure to full sunlight which provides greater versatility for its use in landscaping.

DESCRIPTION OF THE PHOTOGRAPHS

DETAILED DESCRIPTION OF THE PLANT

Figure 1:
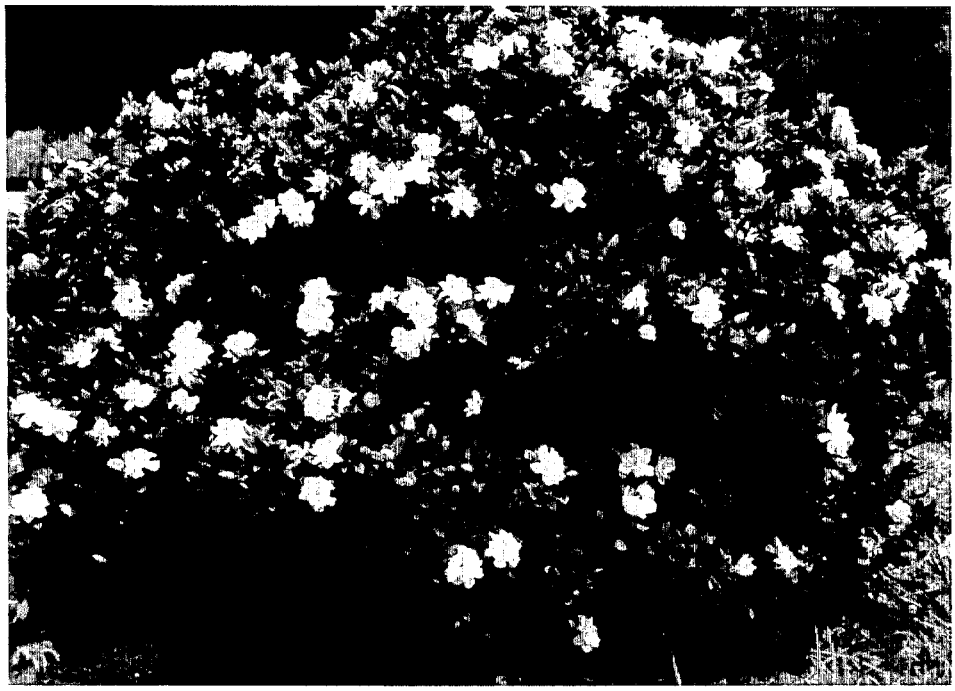
FIG. 1 illustrates the Chuck Hayes Gardenia plant in June bloom.
Figure 3:
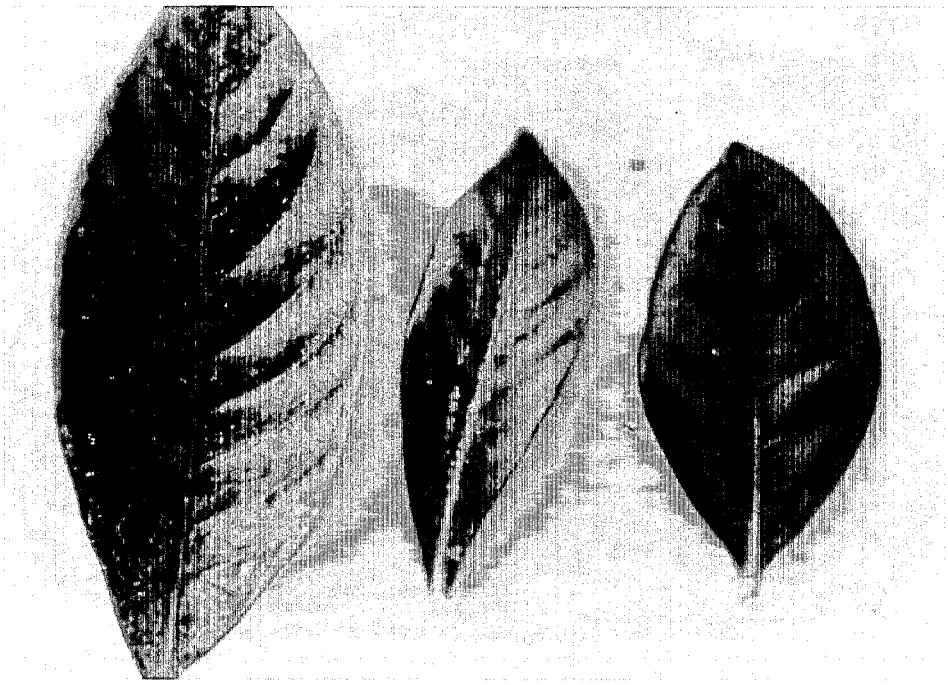
FIG. 3 illustrates the size and shape of an average Chuck Hayes Gardenia leaf (left) compared to an average "Mystery" leaf (middle) and an average large leaf variety gardenia seedling leaf (right).
Figure 2:
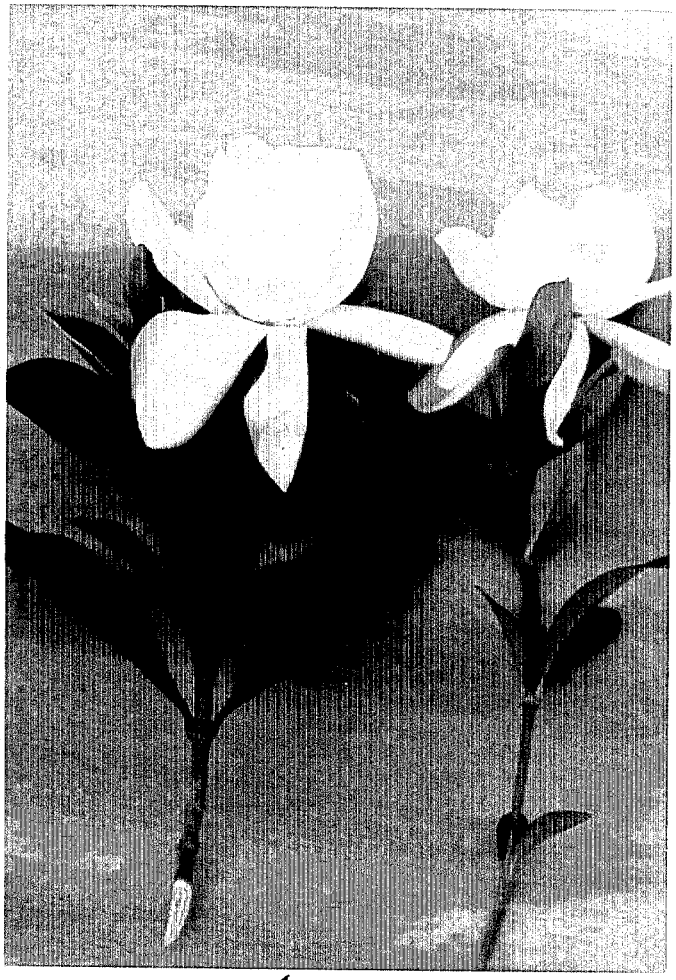
FIG. 2 illustrates a Chuck Hayes Gardenia bloom (left) compared to a "Mystery" bloom (right)

The following is a detailed description of the new variety of *Gardenia jasminoides* as observed and measured at the Hampton Roads Agricultural Experiment Station, Virginia Beach, Va.

Type: The Chuck Hayes Gardenia is a hardy outdoor flowering shrub for garden decoration and landscaping use. A mature plant reaches a height of approximately four feet. The bark, leaf and flower color are typical of the species. The bark is thin, smooth and green turning grey with age as is typical of the species.

Parengate: One parent of the Chuck Hayes Gardenia is believed to be a single flowered strain of *Gardenia jasminoides* which is resistant to cold. The specific parent plant or seed, however, is unknown.

Class: *Gardenia jasminoides.*

Foliage:

*Type.*—Evergreen. The Chuck Hayes Gardenia has leaf shapes varying from narrow lanceolate to broad, short and obovate green leaves. The leaves are borne in opposing pairs.

*Size.*—A fully developed leaf on a main stem has a length of approximately one to two inches on a mature plant and three inches on a young plant, and a width of ¾ to one inch.

*Appearance.*—Short, broad leaves and short stems give the Chuck Hayes Gardenia a more compact and less coarse appearance than larger leafed varieties of gardenia.

Flowers:

*Blooming habits.*—The Chuck Hayes Gardenia blooms continuously during active growth unless interrupted by flower bud abortion. Spring growth matures into flowers for 3 to 4 weeks in June. July and a portion of August weather is hot enough to abort buds. The return of cool weather causes a resumption of flowering during the fall, i.e., during September through to the October frost.

*Bud.*—A Chuck Hayes Gardenia bud is approximately 1¾ to 2 inches in length and ⅝ to ¾ of an inch in diameter. The bud is generally a leaf green color which progresses into white as it opens to a flower. The bud is tapered from the peduncle to its enlarged midlength and is tapered to a rounded point (fusiform). The rounded end is spirally marked with petal edges. The tapered end has ribs ending in sepals at midlength. The bud generally has six sepals. The sepals remain relatively linear with the floral axis and form an end view resembling a six pointed star.

*Bloom.*—The Chuck Hayes Gardenia is double-flowered. A series of outer petals extend radially to form a two to three inch diameter. A series of inner petals stand progressively more vertical to provide a 1½ to 2 inch depth to the flower. The flower's corolla is broadly salverform. Petals forming the outer corolla are somewhat curled and twisted. Petals forming an inner staminoid are fused to the inner surface of the salverform portion of the corolla, and are broadly oval and progressively smaller toward the center producing a double flower. The Chuck Hayes Gardenia has broader staminoid petals than other varieties of gardenia. Flowers on the Chuck Hayes Gardenia are borne between opposing side shoots during periods of growth. The flowers face upward and outward in full bloom.

*Color.*—Waxy, white.

*Petals.*—The petals of the Chuck Hayes Gardenia are ovoid, waxy and thick. The Chuck Hayes Gardenia petals are broader than the petals of other varieties of gardenia.

*Pistils.*—Styles of the Chuck Hayes Gardenia flower are filamentous and inconspicuous when present. Ovaries, borne in a fleshy fruit formed from expansion of a ribbed receptacle below calyx lobes of the flower, form slightly flattened, tan colored seeds of approximately ⅛ of an inch in diameter.

*Stamens.*—Stamens are approximately ¾ of an inch in length with clear to white filaments ending in a yellow anther. The Chuck Hayes Gardenia anthers are rarely visible in the mature flower except in late fall because they are incompletely developed. Since the Chuck Hayes Gardenia is semidouble, a few stamens may be found at the center of the flower. Spring flowers are almost completely devoid of stamens, but fall flowers may have a few well formed stamens apparently bearing fertile pollen since a few fruit may form from these late flowers when no other flowers are available for pollination.

*Fruit.*—Ripe fruits are orange and approximately ¾ of an inch in diameter. The Chuck Hayes Gardenia generally does not develop fruit.

*Fragrance.*—Classically gardenia. A very powerful and pleasing fragrance.

I claim:

1. A new and distinct cultivar of *Gardenia jasminoides* named Chuck Hayes Gardenia, substantially as shown and described herein and characterized by:

(a) a resistance to cold temperatures as low as −5° F.;
(b) a tolerance of evening temperatures as high as 70° F. during blooming periods;
(c) a more compact appearance and growth habit than *Gardenia jasminoides* "Mystery"; and
(d) longer and more floriferous blooming cycles in June and September as compared to *Gardenia jasminoides* "Mystery".

* * * * *